United States Patent
Oshima et al.

(10) Patent No.: US 8,810,410 B2
(45) Date of Patent: Aug. 19, 2014

(54) ACTIVITY METER

(75) Inventors: Yoshitake Oshima, Kyoto (JP); Naoki Takeishi, Toyonaka (JP); Hiroshi Ogawa, Nara (JP); Yuji Asada, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 0 days.

(21) Appl. No.: 13/985,088

(22) PCT Filed: Nov. 28, 2011

(86) PCT No.: PCT/JP2011/077367
§ 371 (c)(1),
(2), (4) Date: Aug. 13, 2013

(87) PCT Pub. No.: WO2012/117632
PCT Pub. Date: Sep. 7, 2012

(65) Prior Publication Data
US 2013/0325358 A1    Dec. 5, 2013

(30) Foreign Application Priority Data

Mar. 1, 2011 (JP) ................. 2011-043762

(51) Int. Cl.
G08B 23/00 (2006.01)
A61B 5/11 (2006.01)
G06F 19/00 (2011.01)
G01C 22/00 (2006.01)
A61B 5/00 (2006.01)

(52) U.S. Cl.
CPC .............. *G06F 19/70* (2013.01); *A61B 5/6823* (2013.01); *A61B 5/1118* (2013.01); *A61B 5/742* (2013.01); *G01C 22/006* (2013.01); *A61B 2562/0219* (2013.01); *A61B 5/6831* (2013.01); *Y10S 128/904* (2013.01)
USPC ......................... 340/573.1; 128/904; 600/300

(58) Field of Classification Search
USPC ......... 340/573.1; 128/904, 2.07; 702/19, 141; 434/127; 482/3, 8; 705/2, 3; 600/300, 600/485, 500, 592, 595; 455/73
See application file for complete search history.

(56) References Cited

U.S. PATENT DOCUMENTS 5,615,685 A * 4/1997 Suga .............................. 600/300
6,010,452 A * 1/2000 Harcourt ....................... 600/300
(Continued)

FOREIGN PATENT DOCUMENTS

JP    2001-258870 A    9/2001
JP    2006-204446 A    8/2006
(Continued)

OTHER PUBLICATIONS

Official Communication issued in International Patent Application No. PCT/JP2011/077367, mailed on Jan. 24, 2012.

*Primary Examiner* — Brent Swarthout
(74) *Attorney, Agent, or Firm* — Keating & Bennett, LLP (57) ABSTRACT

A pedometer includes an activity amount acquisition unit that acquires an activity amount of a user, an index acquisition unit that acquires an index relating to the activity amount, and an index output unit that outputs the acquired index. The index acquisition unit includes an activity age acquisition unit that acquires an activity age represented by a standard age of a person who does the same amount of activity as the activity amount acquired in a unit period, using body information of the user, and acquires an index enabling the active age to reach a target activity age, based on the acquired activity amount.

6 Claims, 8 Drawing Sheets

(56) References Cited

U.S. PATENT DOCUMENTS

| | | | |
|---|---|---|---|
| 6,478,736 B1* | 11/2002 | Mault | 600/300 |
| 6,902,513 B1* | 6/2005 | McClure | 482/8 |
| 7,273,453 B2* | 9/2007 | Shallenberger | 600/300 |
| 2011/0087137 A1* | 4/2011 | Hanoun | 600/587 |
| 2011/0226035 A1 | 9/2011 | Date | |

FOREIGN PATENT DOCUMENTS

| | | |
|---|---|---|
| JP | 2010-017525 A | 1/2010 |
| JP | 2010-167275 A | 8/2010 |
| JP | 2010-253204 A | 11/2010 |

* cited by examiner

ACTIVITY METER

BACKGROUND OF THE INVENTION

1. Field of the Invention

The present invention relates to an activity meter that measures an amount of physical activity of a user, and more particularly to an activity meter that outputs an index relating to the amount of physical activity.

2. Description of the Related Art

For activity meters, JP 2006-204446A and JP 2001-258870A describe methods for measuring the exercise intensity of physical activity or the calories burned during physical activity utilizing an acceleration sensor. With the activity meter of JP 2006-204446A, a standard deviation Sw of acceleration in a fixed time period tw is computed from the output signal of the acceleration sensor, and an exercise intensity wi is computed from the standard deviation Sw using a conversion equation formulated in advance. Also, with the device of JP 2001-258870A, the impulse of momentum is calculated by vector synthesis from tri-axial acceleration, and energy expenditure is calculated from the impulse in response to the type of exercise. The type of exercise is determined based on the ratio of the impulse calculated by vector synthesis and the impulse in the depth, horizontal and vertical directions.

In JP 2010-17525A, whichever age activity pattern that the user's state of activity is equivalent to is computed by comparing the energy expenditure history with reference data.

There are calls among users of activity meters for an index of the amount of physical activity to be presented in comparison with other users, to avoid becoming complacent about the amount of physical activity they do. In this regard, although the activity meters of JP 2006-204446A and JP 2001-258870A output the user's activity amount as calories burned, it is unclear whether the amount of calories burned is high or low or to what age group that amount of calories burned is equivalent.

Although the age activity pattern to which the user's state of activity is equivalent is computed in JP 2010-17525A, an index relating to activity for attaining a target activity pattern is not presented.

SUMMARY OF THE INVENTION

Preferred embodiments of the present invention provide an activity meter that outputs an index to attain a target activity age.

A preferred embodiment of the present invention is provided with an activity amount acquisition unit that acquires an activity amount of a user, an index acquisition unit that acquires an index relating to the activity amount, and an index output unit that outputs the acquired index. The index acquisition unit includes an activity age acquisition unit arranged and programmed to acquire an activity age represented by a standard age of persons who do the same amount of activity as the activity amount acquired in a unit period, using body information of the user, and acquires an index that enables the active age to reach a target activity age, based on the acquired activity amount.

A preferred embodiment of the present invention is able to acquire and output an index to attain a target activity age, based on an activity amount acquired from a user.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Hereinafter, preferred embodiments of the present invention will be described in detail with reference to the drawings. Note that the same or corresponding portions in the following preferred embodiments are given the same reference signs in the drawings, and description thereof will not be repeated.

In the present preferred embodiments, "activity age" represents the standard (or average) age of persons who do the same amount of activity in a unit period as an aggregate activity amount represented by exercise intensity, calories burned or the like, for activity done in the same period. Here, the unit period is preferably 1 day, for example, but is not limited to 1 day and could be any other desirable unit of time.

Also, "real age" preferably indicates calendar age (age counted from the time of birth).

In the present preferred embodiment, METs (Medical Evangelism Training & Strategies) are preferably used as an index indicating physical activity intensity. METs correspond to a unit representing the intensity of physical activity in multiples of a resting state, with sitting down quietly being equivalent to 1 METs and normal walking being equivalent to 3 METs.

Also, "exercise (Ex)" is preferably a unit representing the amount of physical activity, and is obtained by multiplying the intensity of physical activity (METs) by the implementation time period (time: hours) of physical activity.

In an exemplary preferred embodiment of the present invention, a pedometer is illustrated as the activity meter, but the activity meter is not limited to being a pedometer and could be any other desirable device. In other words, the activity meter can be any device having a function capable of measuring the activity amount resulting from physical activity including exercise (includes walking) and daily activities (e.g., vacuuming, carrying items, cooking, etc.). Although a pedometer can be shared by two or more persons, it is assumed here for ease of description that the pedometer is used by one person.

Figure 1:
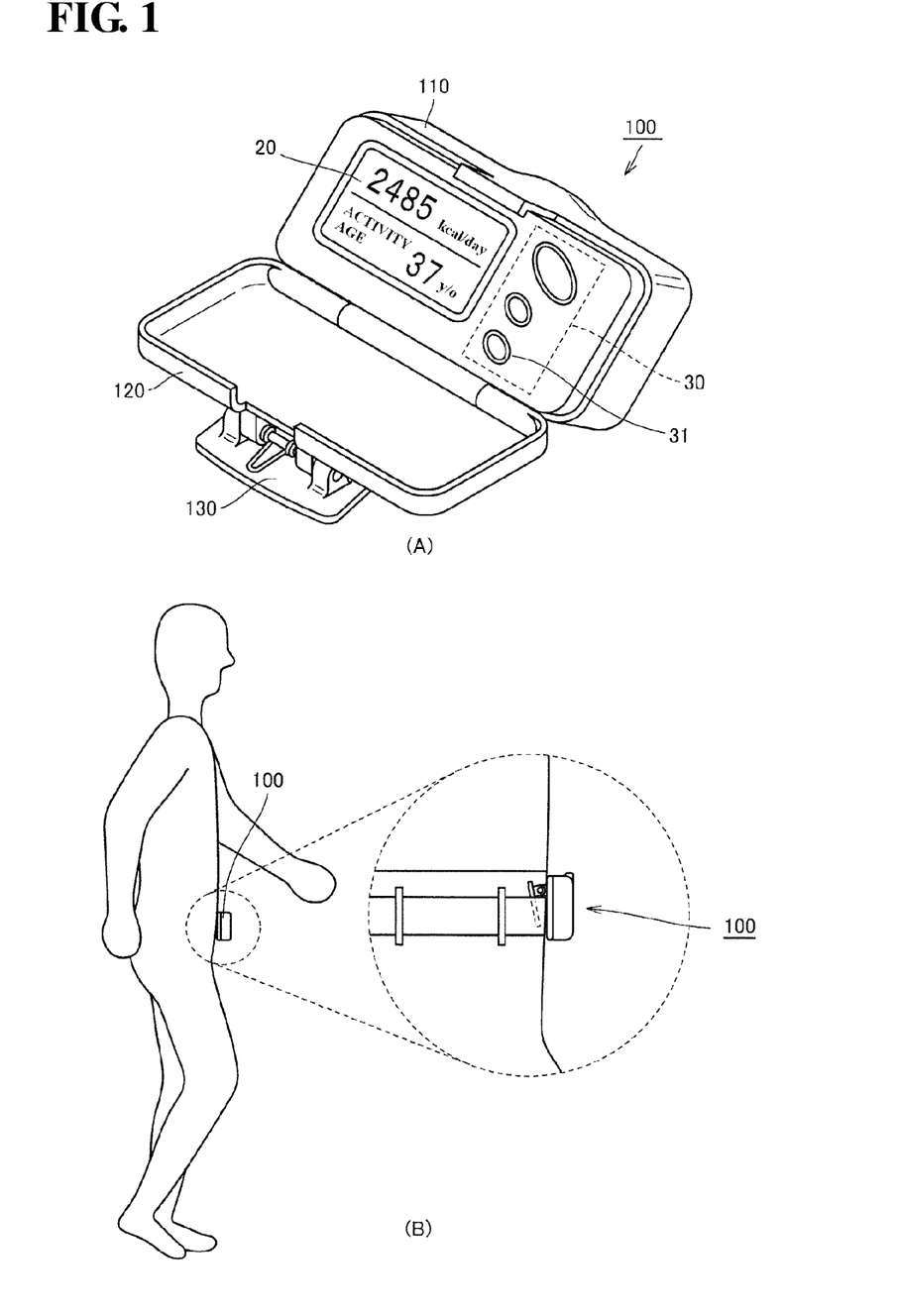
FIGS. 1A and 1B are diagrams illustrating an external appearance and a mode of wearing a pedometer according to a preferred embodiment of the present invention.

Referring to FIG. 1A, a pedometer 100 serving as an activity meter preferably includes a compact main body casing that is portable, and the main body casing is divided into a case main body 110, a cover body 120 and a clip body 130.

The case main body 110 preferably includes a display surface on which is provided a display 20 capable of displaying various information such as the counted number of steps, exercise intensity and activity age, and an operation unit 30 including various buttons arranged to receive operations by the user. The operation unit 30 includes a button 31 that the user operates in order to request output of the activity age.

The bottom end of the case main body 110 and the cover body 120 are preferably rotatably coupled around a joining portion, and the pedometer 100 is opened and closed by rotation of this joining section. The clip body 130 is preferably provided on an opposite surface of the cover body 120 to the surface facing the display surface of the case main body 110. The clip body 130 enables the pedometer 100 to be worn, for example, on the user's waist, abdomen, or the like as shown in FIG. 1B.

Figure 2:
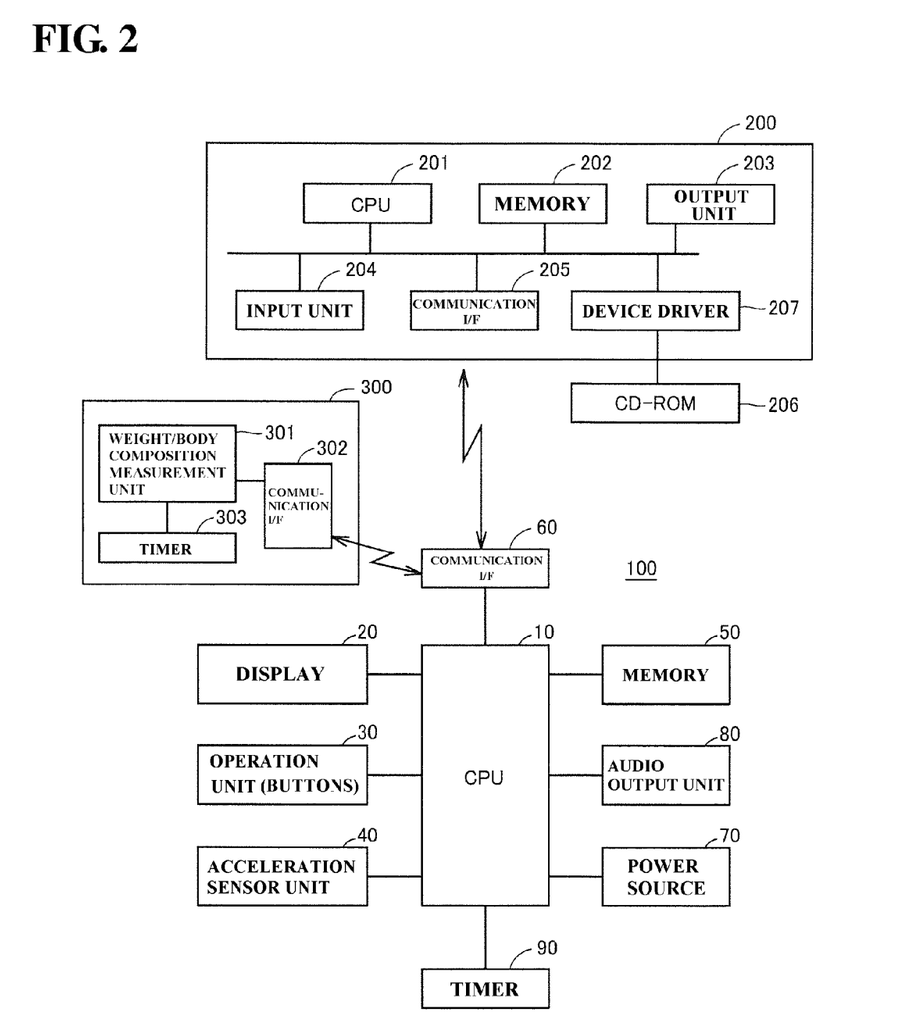
FIG. 2 is a diagram showing the hardware configuration of a system according to a preferred embodiment of the present invention.

The hardware configuration of a system including the pedometer 100 is shown in FIG. 2. The pedometer 100 preferably includes a CPU (Central Processing Unit) 10 arranged and programmed to perform overall control, the display 20, the operation unit 30, an acceleration sensor unit 40 including an acceleration sensor and an MPU (Micro-Processing Unit), a memory 50 arranged to store programs that are executed by the CPU 10, data and the like, a communication I/F (abbreviation of "interface") 60 arranged to perform wireless or wired communication with an external device, a power source 70 such as, for example, a battery, an audio output unit 80 arranged to output audio, and a timer 90 that measures time and outputs time data.

The pedometer 100 preferably performs wireless or wired communication with external devices 200 and 300 via the communication I/F 60. The device 200 is preferably equivalent to a mobile terminal (PDA (Personal Digital Assistant), mobile phone, etc.), for example, and the device 300 preferably has a function of measuring the user's weight and the body composition.

The device 200 preferably includes a CPU 201, a memory 202, an output unit 203, an input unit 204, a communication I/F 205, and a device driver 207 arranged and programmed to access the data of a CD-ROM (Compact Disk Read Only Memory) 206. The device driver 207 preferably includes the CD-ROM 206 removably loaded therein, and reads out data (including programs) from the loaded CD-ROM 206 or writes data to the loaded CD-ROM 206.

The device 300 preferably includes a weight/body composition measurement unit 301 that measures the user's height, weight, body fat, and the like, a communication I/F 302 arranged to transmit measured information to outside the device, and a timer 303. Measured weight and body composition information is transmitted to the pedometer 100 via the communication I/Fs 302 and 60, as weight data and body composition data to which time data indicating the measurement time clocked by the timer 303 is respectively added.

Figure 3:
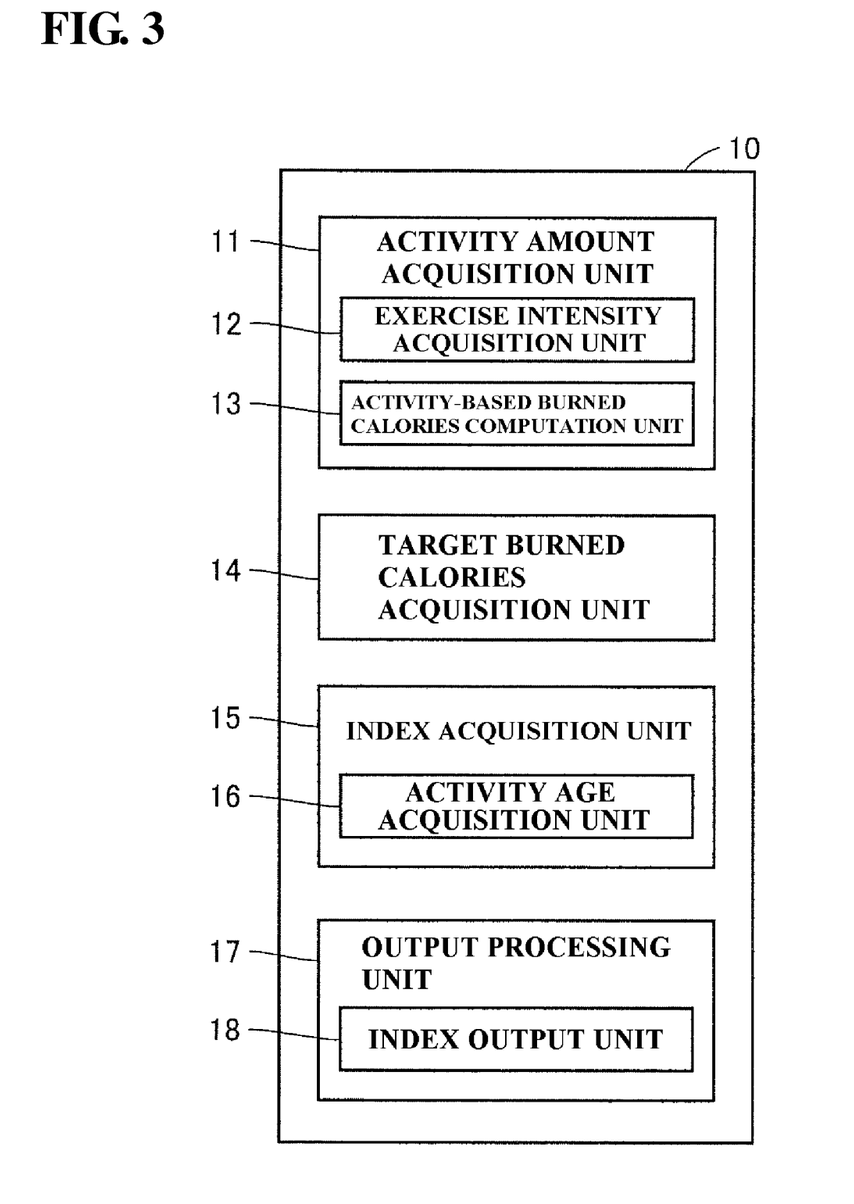
FIG. 3 is a diagram showing the functional configuration of a pedometer according to a preferred embodiment of the present invention.

The configuration of functions that operate under the control of the CPU 10 is shown in FIG. 3. The functions preferably include an activity amount acquisition unit 11 arranged and programmed to acquire the amount of physical activity of the user, a target burned calories acquisition unit 14 arranged and programmed to acquire a target amount of calories burned by a person of a target activity age in a unit period, an index acquisition unit 15 arranged and programmed to acquire an index relating to the activity amount, and an output processing unit 17 that is arranged and programmed to output various information.

The activity amount acquisition unit 11 preferably includes an exercise intensity acquisition unit 12 arranged and programmed to acquire the exercise intensity of the user, and an activity-based burned calories computation unit 13 arranged and programmed to compute the amount of calories burned based on the activity amount. The index acquisition unit 15 preferably includes an activity age acquisition unit 16 arranged and programmed to acquire the activity age. The output processing unit 17 preferably includes an index output unit 18 arranged and programmed to output an index relating to the activity amount to the user.

The units in FIG. 3 may be implemented by a program provided on a non-transitory computer readable medium and to be executed by computer or processing device, by a combination of a program and a circuit module, or entirely by hardware, for example.

The activity amount acquisition unit 11 receives input of exercise intensity from the acceleration sensor unit 40 and input of time data from the timer 90. Activity intensity data Mi (discussed later) obtained by associating activity intensity indicating the exercise intensity from the acceleration sensor unit 40 and the time data from the timer 90 is acquired, and the acquired activity intensity data Mi is stored in the memory 50. The time data associated with the activity intensity indicates the implementation date and time of the measured activity.

The acceleration sensor unit 40 measures the number of steps in a manner similar to a measurement of the number of steps performed by a generic pedometer. The acceleration sensor detects acceleration applied to the pedometer 100. The detected acceleration is preferably derived as a voltage signal. The MPU processes the output signal from the acceleration sensor. For example, the MPU performs processing so as to count each time an acceleration of greater than or equal to a threshold is detected as one step, based on the signal output sequentially from the acceleration sensor.

Computation of Exercise Intensity

The measurement operation performed by the MPU of the acceleration sensor unit 40 preferably involves computing the exercise intensity (unit: METs) for each predetermined time period, using acceleration data measured based on the acceleration signal input from the acceleration sensor, at predetermined time intervals (e.g., 20-second intervals, etc.) defined in advance. As a specific computation method, the exercise intensity can be computed using a well-known technique, such as, for example, the technique disclosed in JP 2009-028312A.

Exercise intensity is an index representing the intensity of physical activity that depends on walking pitch (number of steps for each predetermined time period) and the height of the user that is input in advance. For example, a resting state is equivalent to 1 METs, walking normally (4 km/h) is equivalent to 3 METs, vacuuming is equivalent to 3.5 METs, and jogging is equivalent to 7 METs (see: Exercise and Physical Activity Guide for Health Promotion "Exercise Guide 2006" (Ministry of Health, Labour and Welfare)).

Computation of Calories Burned

The activity-based burned calories computation unit 13 preferably computes the calories burned by the activity of the user according to the following equation: calories burned (kcal)=exercise intensity (METs)×weight (kg)×exercise duration (h)×1.05 (See: Exercise and Physical Activity Guide for Health Promotion "Exercise Guide 2006", Ministry of Health, Labour and Welfare). Exercise intensity and exercise duration can be acquired from the activity intensity data Mi, and weight can be acquired from physique data 57, discussed later.

Also, the activity amount acquisition unit 11 preferably computes the amount of physical activity (unit: Ex), by multiplying the activity intensity (METs) by the implementation time period (time: hours) of physical activity.

The activity age acquisition unit 16 acquires an activity age, based on the activity amount of the user. The activity age can be computed through conversion using an arithmetic equation, or can be acquired by searching a conversion table.

The conversion equation that is used in computing the activity age preferably includes parameters (variables) and coefficients. The parameters include, for example, body information having the basal metabolic rate of the user. The activity age acquisition unit 16 is able to variably set the coefficients.

Figure 4:
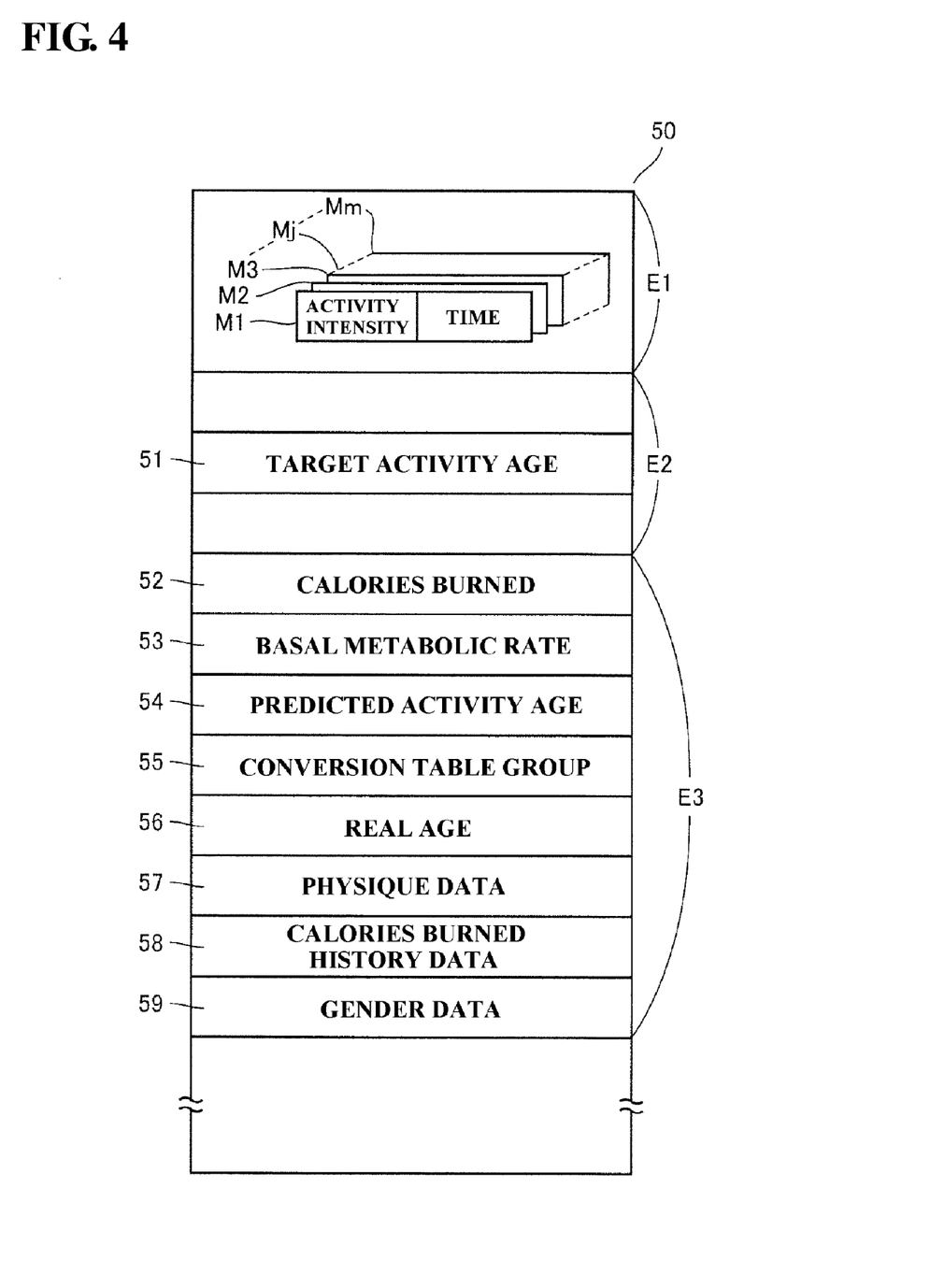
FIG. 4 is a diagram showing exemplary memory content of a memory according to a preferred embodiment of the present invention.

The storage content of the memory 50 is illustrated in FIG. 4. Referring to FIG. 4, the memory 50 preferably includes an area E1 where the activity intensity data Mi (i=1, 2, 3, ... j, ... m) is stored, an area E2 where a target activity age 51 indicating the target activity age set by the user operating the operation unit 30 is stored, and an area E3. The activity intensity data Mi includes activity intensity measured by daily activities or exercise, and the corresponding measurement time period.

The area E3 preferably includes calories burned 52 computed from the activity amount of the user, a computed basal metabolic rate 53, an acquired predicted activity age 54, and a conversion table group 55 that is referenced in order to convert calories burned into an activity age stored therein. Also preferably stored therein is real age data 56 of the user, physique data 57 including the user's weight, height, and the like, calories burned history data 58 indicating the time series change in calories burned, and gender data 59 indicating the user's gender. Body information representing unique physical characteristics of the user preferably includes the real age data 56, the physique data 57, the gender data 59, the basal metabolic rate 53 and the like.

Figure 5:
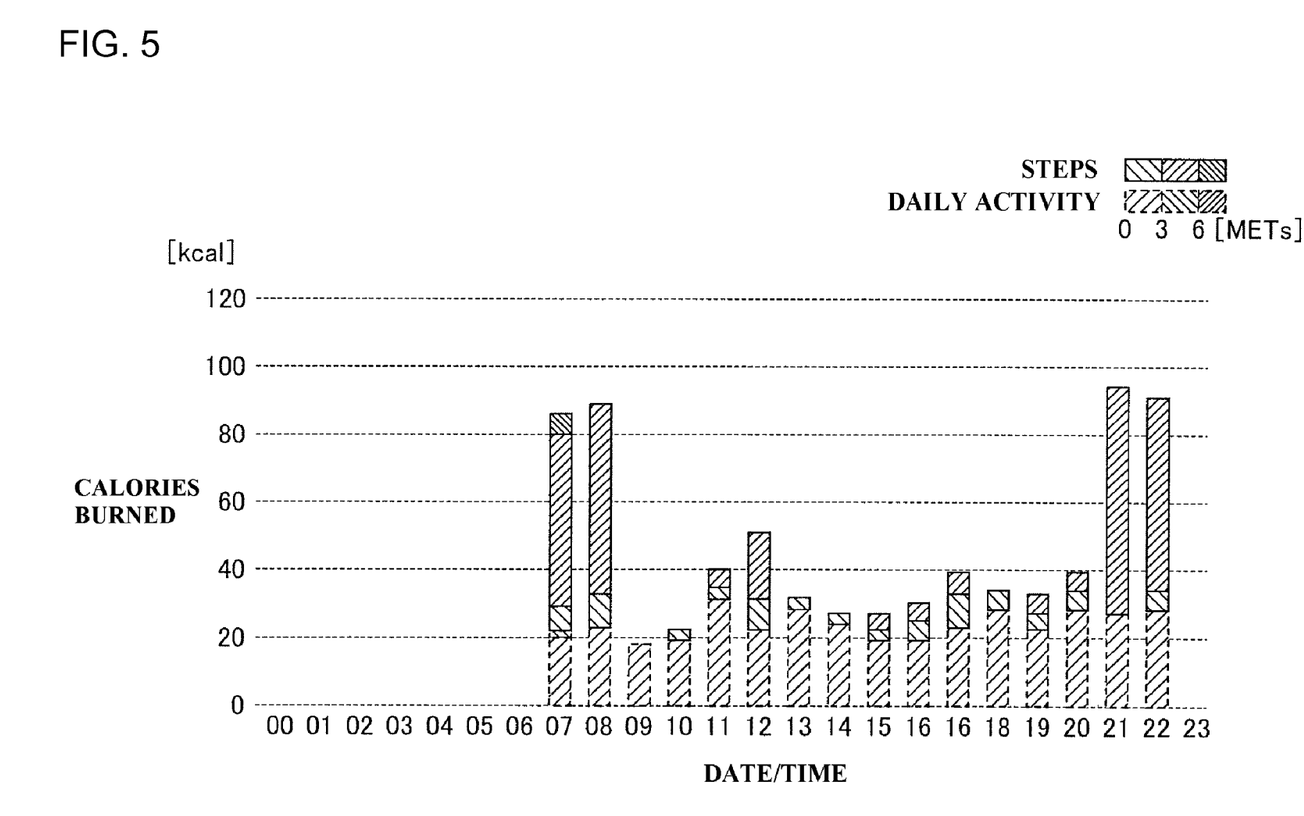
FIG. 5 is a graph showing the change in calories burned by a user according to a preferred embodiment of the present invention.

In FIG. 5, calories burned (kcal) by the user for each unit time slot (here, 1 hour time slots) in the unit time period are shown with a bar graph. The data in FIG. 5 represents an example of the calories burned history data 58 of the area E3. The calories burned history data 58 is generated by the activity-based burned calories computation unit 13. Specifically, the activity-based burned calories computation unit 13 computes, based on the activity intensity data Mi for the past one month, for example, the average value for one month of activity intensity for each unit time slot of 1 day (hourly at 0:00, ... 7:00, 8:00, ... 22:00, ... 24:00). The activity-based burned calories computation unit 13 then computes, in accordance with the abovementioned equation that uses the average value for each unit time period, the calories burned for the unit time period. The average calories burned for the past one month for each unit time period computed in this way is called "unit calories burned". The activity-based burned calories computation unit 13 stores the computed unit calories burned in the area E3 in association with the corresponding unit time period as the calories burned history data 58.

The calories burned history data 58 is preferably updated daily, for example, but could be updated according to other time periods. The activity-based burned calories computation unit 13 computes the unit calories burned daily at 24:00, for example, and updates the calories burned history data 58 using the computation result.

Here, although the length of the unit time slot is preferably set to 1 hour, the length is not limited to 1 hour and could instead be any other desirable length of time. Also, although average calories burned for each unit time period is stored, the calories burned that is stored is not limited to an average value, and may be a representative value, such as the mode or median, for example.

Computation of Activity Age

The procedure to compute the activity age performed by the activity age acquisition unit 16 will now be described.

First, derivation of the equation that forms the basis for computing the activity age will be described. The theoretical basal metabolic rate of the user for 1 day can be computed with equation 1.

$$\text{theoretical basal metabolic rate} = (0.0481 \times W + 0.0234 \times H - 0.0138 \times R - 0.5473 \times F + 0.1238) \times 239 \quad \text{(eq. 1)}$$

Here, W denotes weight, H denotes height, R denotes real age, and F denotes gender. Weight W is denoted in kilograms (kg) and height H is denoted in centimeters (cm). F is 1 if the gender is male and is 2 if the gender is female. In accordance with equation 1, real age: R can be represented by equation 2.

$$R = (\text{theoretical basal metabolic rate}/239 - 0.1238 - 0.0481 \times W - 0.0234 \times H + 0.5473 \times F)/(-0.0138) \quad \text{(eq. 2)}$$

Here, the physical activity level PAL of the user for 1 day can be computed from the aggregate calories burned (unit: kcal) for 1 day/basal metabolic rate (unit: kcal) for 1 day, and that the physical activity level PAL is 1.6 to 1.9 for a "normal" amount of activity. Here, the intermediate value 1.75 is preferably used as the representative value. Accordingly, because a relational equation: aggregate calories burned [kcal/day] at standard level=theoretical basal metabolism value [kcal/day]×1.75 is satisfied, relative basal metabolic rate=actual aggregate calories burned/1.75 (eq. 3) can be derived from this relational equation, in order to derive the activity age of the user. In accordance with equations 1 to 3, equation 4, which is a basic equation for computing activity age, can be derived.

$$\text{Activity age[age]} = \{(\text{actual aggregate calories burned} [\text{kcal/day}]/1.75)/239 - 0.1238 - 0.0481 \times W - 0.0234 \times H + 0.5473 \times F\}/(-0.0138) \quad \text{(eq. 4)}$$

The weight W and height H in equations 1 to 4 are indicated by the physique data 57 that is read out from the memory 50, and the gender F is similarly indicated by the gender data 59 that is read out from the memory 50.

The activity age may be acquired by searching the conversion table group 55, instead of the arithmetic operation using equation 4. Here, the conversion table group 55 preferably includes a conversion table for each set of height H, weight W, and gender F. In the conversion table corresponding to each set, activity ages are stored in association with respective basal metabolic rates computed in accordance with equation 3.

Figure 6:
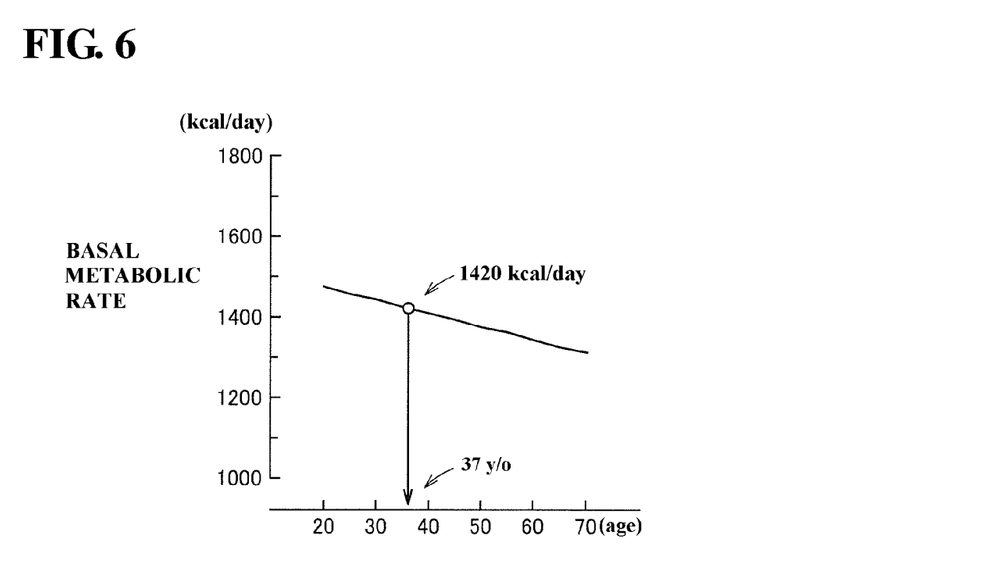
FIG. 6 is a diagram showing an example of a conversion table according to a preferred embodiment of the present invention.

An exemplary conversion table is shown in FIG. 6. In FIG. 6, a conversion table in the case where the height, weight, and gender of the user are respectively 170 cm, 60 kg and male is shown as a linear function graph in which activity age is shown on the horizontal axis and basal metabolic rate computed by equation 3 is shown on the vertical axis. The activity age acquisition unit 16 searches the conversion table group 55 based on the real age data 56, the physique data 57, and the gender data 59 in the memory 50, and reads out a corresponding conversion table (FIG. 6). Also, the activity age acquisition unit 16 computes the basal metabolic rate from the aggregate calories burned computed by the activity-based burned calories computation unit 13. For example, if the aggregate amount of calories burned is 2485 kcal, the basal metabolism is computed by equation 3 to be 1420 kcal. Searching the conversion table of FIG. 6 based on the basal metabolic rate (1420 kcal) enables the activity age acquisition unit 16 to acquire 37 years old as the activity age.

Note that the conversion table in FIG. 6 was computed on the basis of Ganpule AA, et al. Interindividual variability in sleeping metabolic rate in Japanese subjects, European Journal of Clinical Nutrition (2007), pp. 1-6.

Processing Flowchart

Figure 7:
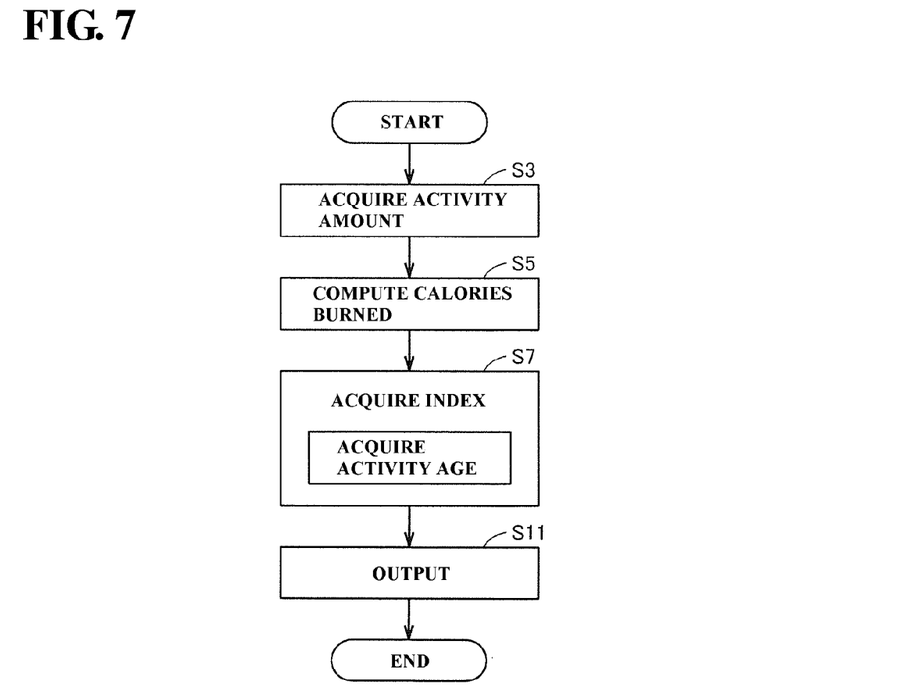
FIG. 7 is a flowchart of processing according to a preferred embodiment of the present invention.

A processing flowchart according to a preferred embodiment of the present invention is shown in FIG. 7. Processing in accordance with this processing flowchart is realized by the CPU 10 reading out a predetermined program from the memory 50 and executing the respective instructions of the read program. Computation of the user's activity age will be described in accordance with the flowchart in FIG. 7.

Note that it is assumed that the user basically carries the pedometer 100 with them from when they get up until when they go to bed, or in other words, for the period from 7:00 to 22:00. Accordingly, it is assumed that a sufficient number of sets of activity intensity data Mi are stored in the area E1 of the memory 50.

Presentation of Activity Age Based on Calories Burned for 1 Day

When the user operates the button 31 of the operation unit 30 at bedtime in the case of wanting to know his or her activity age based on the activity amount for 1 day, the CPU 10 receives the user operation. Specifically, the CPU 10 starts the processing of FIG. 7, based on the operation signal that is output from the operation unit 30 as a result of the button 31 being operated. When the processing is started, the activity amount acquisition unit 11 acquires the activity amount for the current day, that is, the actively amount from 00:00 that day up until the current point in time (22:00), based on the activity intensity data Mi read out from the area E1 of the memory 50 (step S3). Next, the activity-based burned calories computation unit 13 computes the calories burned by the user, based on the acquired activity amount (step S5), and the activity age acquisition unit 16 computes the user's basal metabolic rate for the unit period (step S7).

The activity age acquisition unit 16 computes the activity age in accordance with equation 4, using the computed calories burned and basal metabolic rate (step S7). Alternatively, the activity age is acquired by searching a conversion table. The activity age acquisition unit 16 provides the acquired activity age to the output processing unit 17. The index output unit 18 of the output processing unit 17 displays the provided activity age on the display 20, or outputs the provided activity age via the audio output unit 80 (step S11).

An exemplary display on the display 20 at this time is shown in FIG. 1A. In FIG. 1A, the acquired activity age is preferably displayed together with the computed calories burned. If the displayed activity age indicates the real age or is judged to be close to the real age, the user can be made aware that the amount of activity (exercise) is appropriate, and if judged to greatly exceed the real age, the user can be made aware that the amount of activity (exercise) is insufficient.

Figure 8:
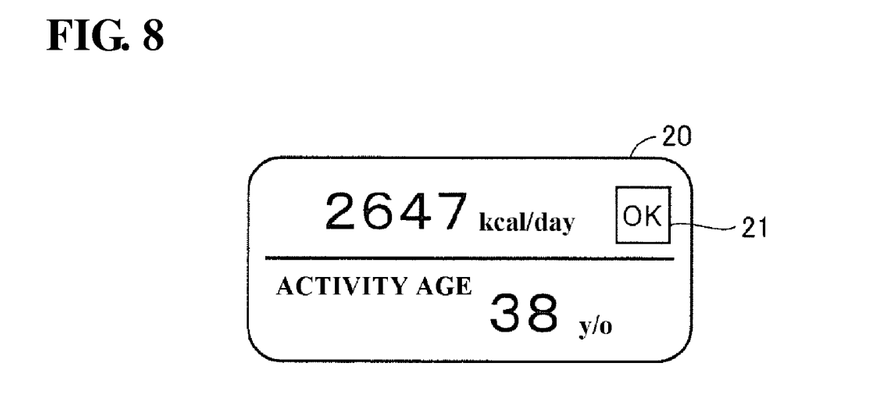
FIG. 8 is a diagram showing an exemplary display of activity age according to a preferred embodiment of the present invention.

The activity age may be displayed as shown in FIG. 8. In FIG. 8, an "OK" message 21 is jointly displayed if the activity age is less than or equal to the user's real age, and an "NG" message is jointly displayed if the activity age is greater than the user's real age.

Accordingly, the output in FIG. 1A or in FIG. 8 enables an index used to judge whether the activity amount for 1 day is appropriate to be presented to the user. The user is able to gain the motivation to increase their amount of activity or to maintain their current amount of activity by checking the index.

Here, the processing of FIG. 7 is started in response to the button 31 being operated, but the start timing is not limited thereto, and a configuration may be adopted in which the CPU 10 starts processing when the timer 90 clocks a predetermined time every day, for example.

Presentation of Index based on Target Activity Age

The CPU 10 may be configured to present an activity amount index enabling the activity age to reach the target activity age 51 as an amount of calories that should be burned.

In the present preferred embodiment of the present invention, in the case where the user requests presentation of an index based on target activity age by operating the operation unit 30, the average amount of calories that the user should burn (hereinafter, referred to as "calories burned WC) in 1 week, for example, in order for the activity age to reach the target activity age is computed and output as an activity amount index.

First, the target burned calories acquisition unit 14 preferably computes the calories burned WC in accordance with the abovementioned relational equation: aggregate calories burned [kcal/day] at standard level=theoretical basal metabolic rate [kcal/day]×1.75, the target activity age 51, and the conversion table shown in the graph of FIG. 6. Specifically, the target burned calories acquisition unit 14 searches the conversion table in FIG. 6 based on the target activity age 51 read out from the memory 50, reads out the corresponding basal metabolic rate from the conversion table, computes the value of the aggregate calories burned [kcal/day] at the standard level from the read basal metabolic rate and the abovementioned relational equation, uses this computed value to compute the calories burned WC by (computed value×7 (days)), and outputs the computed calories burned WC. Also, the unit period may be changed from 1 week to 1 day, and the exercise time period (unit: minutes) per day in the case where the user is active at an exercise intensity of 3 METs, for example, may be computed by (computed value/(1.05×3 METs×weight (kg))×60 min/7) and output as the calories burned WC, or the calories that should be burned per day may be computed by WC/7 and output. In this way, the target amount of calories to be burned in 1 day is indirectly presented by the exercise time period (unit: minutes) per day or is directly presented by computing WC/7.

As an alternative presentation mode, the subsequent amount of calories that should be burned or the subsequent activity amount, that is, the subsequent time period for which the user should be active, in order to attain the target age may be presented. The case where 1 week is assumed to be from Sunday to Saturday will be described. In order to simplify the description, the user is assumed to be active at 3 METs.

When the operation unit 30 is operated and a request is input, the activity-based burned calories computation unit 13 preferably computes the calories burned (hereinafter, referred to as "calories burned CC") based on activity from Sunday of the current week up until the current point in time, that is, activity up until the point in time at which the request is input. Specifically, the activity-based burned calories computation unit 13 acquires the activity intensity and the exercise duration, based on the activity intensity data Mi, and computes the calories burned CC in accordance with the abovementioned equation (calories burned (kcal)=exercise intensity (METs)×weight (kg)×exercise duration (h)×1.05).

The index acquisition unit 15 then subtracts the calories burned CC from the calories burned WC. The resultant value represents the calories that should be burned (hereinafter, referred to as "calories burned RC") during the remainder of the week (remaining period from now until the end of the week), and is acquired as an activity amount index. Also, the time period (minutes) that the user should exercise for the current day is preferably computed by (calories burned RC/(remaining days)/(1.05×3 METs×weight (kg))/60 min). The activity amount indices thus computed (calories burned RC and time that the user should exercise for the current day (minutes)) are displayed on the display 20 by the index output unit 18, or are output from the audio output unit 80.

Figure 9:
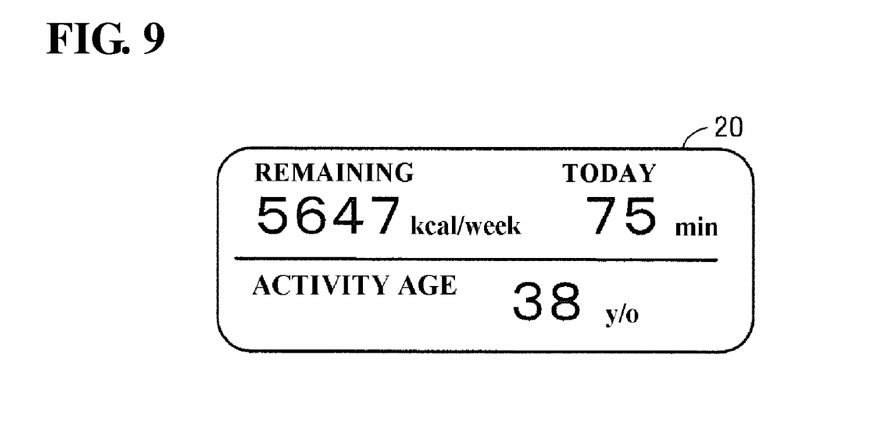
FIG. 9 is a diagram showing an exemplary display of an index relating to target activity age according to a preferred embodiment of the present invention.

Exemplary display on the display 20 in this case is shown in FIG. 9. In FIG. 9, the calories burned RC (5647 kcal), the time period (75 minutes) that the user should exercise for the current day, and the activity age (38 years old) are displayed. The target activity age 51 set by the user may also be jointly displayed.

Presentation of Index based on Predicted Activity Age

The CPU 10 preferably acquires a predicted amount of calories burned for that day from the past calories burned data of the user, computes the activity age to be acquired from the predicted calories burned as the predicted activity age 54, and stores the computed activity age in the area E3 of the memory 50.

In the present preferred embodiment of the present invention, in the case where the user requests presentation of an index based on predicted activity age by operating the operation unit 30, the activity-based burned calories computation unit 13 preferably computes the calories burned based on activity up until the current point in time on that day, that is, activity up until the point in time at which the request is input (hereinafter, referred to as "calories burned TC"). Specifically, the activity-based burned calories computation unit 13 acquires the exercise intensity and exercise duration, based on the activity intensity data Mi for the current day, and computes the calories burned TC in accordance with the above-mentioned equation (calories burned (kcal)=exercise intensity (METs)×weight (kg)×exercise duration (h)×1.05).

Next, the activity-based burned calories computation unit 13 preferably searches the calories burned history data 58 in the area E3 of the memory 50, based on the current time of the timer 90. The activity-based burned calories computation unit 13 then computes, from the search result, the sum of calories burned for each time period after the current time, and adds the summed calories burned to the calories burned TC. The amount of calories burned of the addition result indicates the predicted calories burned for the current day. The index acquisition unit 15 preferably computes the activity age from the predicted calories burned in accordance with the above-mentioned procedure. In this way, it is estimated, from the average calories burned by the user up until the previous day, what the activity age will be if the user spends the current day in the same manner.

The estimated activity age represents the predicted activity age 54 and is stored in the memory 50, as well as being displayed on the display 20 by the index output unit 18 or being output from the audio output unit 80.

Figure 10:
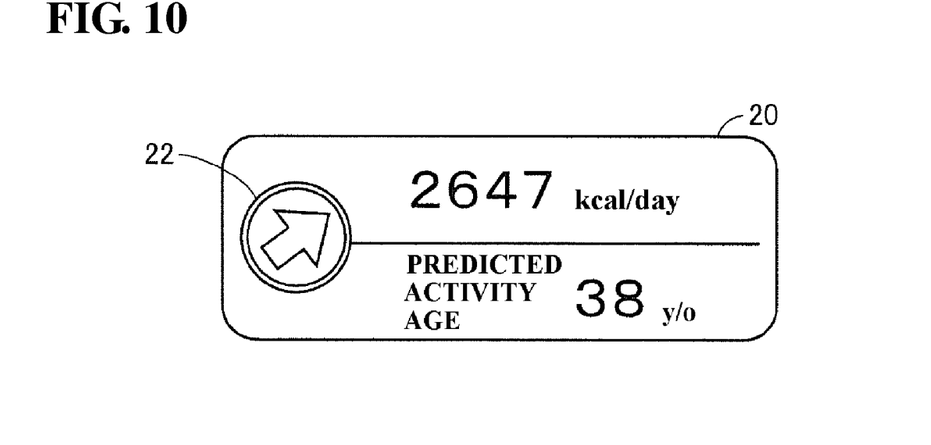
FIG. 10 is a diagram showing an exemplary display of predicted activity age according to a preferred embodiment of the present invention.

An exemplary display on the display 20 in this case is shown in FIG. 10. In FIG. 10, the calories burned TC and the predicted activity age are preferably respectively displayed as 2647 kcal and 38 years old.

Presentation of Activity Pace Index Relative to Predicted Activity Age

The index acquisition unit 15 may acquire an index representing the pace at which the user is burning calories relative to the aggregate calories burned for the predicted activity age. This index is preferably output by, for example, an arrow mark 22 in FIG. 10.

Specifically, the index acquisition unit 15 preferably computes a standard aggregate number of calories burned SC for a person of the predicted activity age from the acquired predicted activity age, the conversion table in FIG. 6, and equation 3. The index acquisition unit 15 then preferably computes the calories burned by the person up until the current point in time. In other words, the index acquisition unit 15 computes the calories burned corresponding to the period from 7:00 up until the current time, based on the period from 7:00 to 22:00, the current time clocked by the timer 90, and the aggregate calories burned SC. The index acquisition unit 15 then preferably compares the computed calories burned (here, standard intermediate calories burned C1) with the calories burned from 7:00 that day up until the current time (here, intermediate calories burned C2) that is computed using the activity intensity data Mi of the user for that day. The index acquisition unit 15 outputs "increase exercise pace" data when it is determined from the comparison result that the condition (C1>C2) is satisfied, and outputs "decrease exercise pace" data when it is determined from the comparison result that the condition (C1<C2) is satisfied.

The index output unit 18 outputs an upward arrow mark 22 based on "increase exercise pace" data that is output from the index acquisition unit 15, and prompts the user to increase his or her exercise pace. Also, the index output unit 18 outputs a downward arrow mark 22 based on "decrease exercise pace" data that is output, and prompts the user to drop his or her exercise pace.

Note that the orientation of the arrow mark 22 may be decided through comparison of the predicted activity age 54 with the target activity age 51 set by the user. In other words, the arrow mark 22 may be angled upward to prompt the user to "increase exercise pace" when the predicted activity age 54 is higher than the target activity age 51, and angled downward to advice the user not to be active at too high a pace when the predicted activity age 54 is lower than the target activity age 51.

Presentation of Activity Age Index based on Daily Pattern

Figure 11:
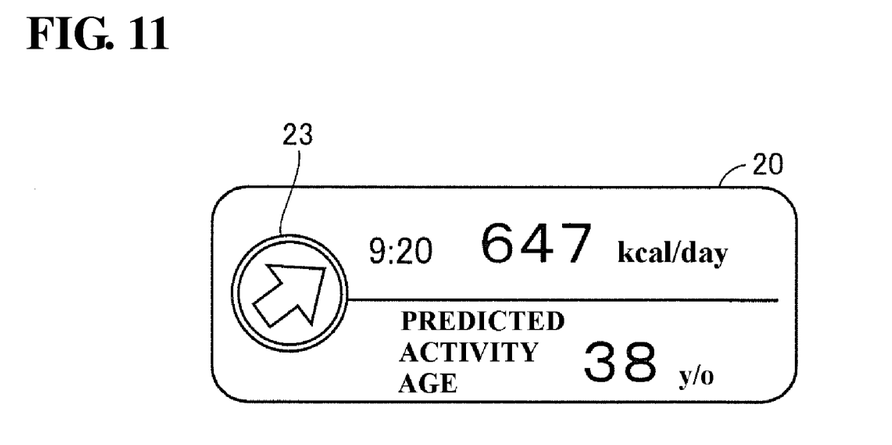
FIG. 11 is a diagram showing an exemplary display conforming to a daily pattern according to a preferred embodiment of the present invention.

The activity amount of a given time slot shown by the calories burned history data 58 that indicates a change in the past calories burned by the user may be compared with the activity amount of the same time slot for the current day, and the index output unit 18 may output an activity-related index based on the comparison result. Exemplary display on the display 20 by the index output unit 18 is shown in FIG. 11. In FIG. 11, the current time (9:20), the calories burned up until the current time (647 kcal), the above-mentioned predicted activity age (38 years old), and an arrow mark 23 are displayed.

Specifically, the index acquisition unit 15 computes the calories burned of the current time slot (9:00 time slot) from the activity intensity data Mi. The index acquisition unit 15 compares the computed calories burned with the calories burned of the same time slot as the current time slot read out from the calories burned history data 58. The arrow mark 23 will be angled upward when the comparison result indicates that the condition: (computed calories burned>read calories burned) is satisfied, and the arrow mark 23 will be angled downward when the condition (computed calories burned<read calories burned) is satisfied.

An activity amount index that indicates whether the calories burned of the time slot to which the current time clocked by the timer 90 belongs is greater than or less than the average calories burned for the same time slot in the past can thus be presented.

Modifications to Preferred Embodiments

Processing relating to the abovementioned indices may be implemented by the device 200. In other words, the device 200 stores the required data of the areas E2 and E3 in the memory 202, and receives the activity intensity data Mi from the pedometer 100. The CPU 201 preferably computes the activity age and various indices with the abovementioned computation procedures using this data, and outputs the computed activity age and indices to the output unit 203 or transmits the computed activity age and indices to the pedometer 100 to be displayed on the display 20.

The activity intensity may be computed by a method using heart rate detected from the user and a predetermined computation equation, instead of being computed by the abovementioned method based on body motion detected in accordance with the acceleration signal.

Also, although the basal metabolic rate is preferably computed using equation 1, the computation method is not limited thereto. For example, the basal metabolic rate may be computed from the body composition information measured by the weight/body composition measurement unit 301. As for the method of computing the basal metabolic rate from body composition information according to the above-described preferred embodiments of the present invention, the basal metabolic rate can be easily computed from fat-free mass measured by the weight/body composition measurement unit 301. In this case, the basal metabolic rate can be computed in accordance with the equation: basal metabolic rate=A× FFM+B (FFM: fat-free mass, A, B: constants).

Other Preferred Embodiments

The method for computing and outputting the activity age described using the abovementioned flowchart can also be provided as a program provided on a non-transitory computer readable medium for execution by a computer or other processing device. The program that realizes the method is preferably stored in the memory 50 of the pedometer 100 in advance, and the processing is realized by the CPU 10 reading out the program from the memory 50 and executing the instruction code. This program may be supplied by being downloaded from an external information processing device including the device 200 to the memory 50 via the communication I/F 60 through a communication line.

Also, the device 200 may store such a program and the data shown in FIG. 4 in the memory 202, the activity age may be computed in the device 200 by the CPU 201 reading out the program from the memory 202 and executing the instruction code, and the computed activity age may be displayed via the output unit 203. The data shown in FIG. 4 can be transmitted from the pedometer 100 to the device 200 via the communication I/F 60. Also, the activity age computed by the device 200 may be transmitted to the pedometer 100 and displayed on the display 20.

To allow the device 200 to compute the activity age, the program is provided to the device 200 as a program product recorded on a non-transitory computer-readable recording medium (not shown) that is preferably included in the device 200 such as a floppy disk, the CD-ROM 206, a ROM (Read Only Memory) of the memory 202, a RAM (Random Access Memory), or a memory card. Alternatively, the program can also be provided by prerecording the program on a non-transitory physical recording medium such as a hard disk (not shown) built into the device 200. Also, the program can also be provided by download to the device 200 from other information processing device via a network.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

The invention claimed is:

1. An activity meter comprising:
    an activity amount acquisition unit arranged and programmed to acquire an activity amount of a user;
    an index acquisition unit arranged and programmed to acquire an index relating to the activity amount; and
    an index output unit arranged and programmed to output the index acquired by the index acquisition unit; wherein
    the index acquisition unit:
        includes an activity age acquisition unit arranged and programmed to acquire an activity age represented by a standard age of a person who does a same amount of activity as an activity amount acquired in a unit period, using body information of the user;
        is arranged and programmed to acquire the index to enable the active age to reach a target activity age, based on the activity amount acquired in the unit period;
        includes a target activity amount acquisition unit arranged and programmed to acquire a target activity amount representing an aggregate amount of activity done in the unit period by a person of the target activity age;
        is arranged and programmed to acquire an index, using the acquired target activity amount;
        compares an activity amount of the user acquired by the activity amount acquisition unit within the unit period with the target activity amount acquired by the target activity amount acquisition unit, and acquires the index based on a comparison result; and
        computes a difference between an intermediate activity amount representing an activity amount from a start of the unit period acquired by the activity amount acquisition unit to partway from the start of the unit period and the target activity amount acquired by the target activity amount acquisition unit, and acquires the index based on a computed difference;
    the unit period includes a plurality of time slots;
    the activity meter further comprises a storage unit arranged to store a representative value for each time slot of the activity amount acquired by the activity amount acquisition unit in association with the time slot; and
    the index acquisition unit:
        includes a predicted activity unit arranged and programmed to acquire a predicted activity amount in the unit period, using the representative value stored for each time slot in the storage unit and the intermediate activity amount; and
        is arranged and programmed to acquire, as the index, a predicted activity age representing an activity age acquired using the acquired predicted activity amount and the body information of the user.

2. The activity meter according to claim 1, wherein the body information includes a basal metabolic rate of the user.

3. The activity meter according to claim 1, wherein
    the activity amount acquisition unit includes a calories burned acquisition unit arranged and programmed to acquire calories burned by the user as the activity amount; and the activity age acquisition unit is arranged and programmed to acquire an activity age represented by a standard age of a person who burns a same amount of calories as calories burned acquired in the unit period, using body information of the user.

4. The activity meter according to claim 3, wherein
the activity amount acquisition unit includes an exercise intensity acquisition unit arranged and programmed to acquire an exercise intensity of the user as the activity amount; and
the calories burned acquisition unit acquires calories burned in the unit period, from the body information and the exercise intensity of the unit period acquired by the exercise intensity acquisition unit.

5. The activity meter according to claim 1, wherein the index acquisition unit is arranged and programmed to:
acquire a standard activity amount of a person of the predicted activity age in the unit period;
compute a standard intermediate activity amount from the start of the unit period to partway from the start, based on the acquired standard amount of intermediate activity; and
compare the computed standard intermediate activity amount with the intermediate activity amount of the user, and to acquire the index based on a comparison result.

6. The activity meter according to claim 1, wherein the index acquisition unit compares the activity amount of the user in a given time slot acquired by the activity amount acquisition unit with the representative value of the corresponding activity amount in the same time slot stored in the storage unit, and acquires the index based on a comparison result.

* * * * *